United States Patent [19]

Polyblank et al.

[11] Patent Number: 5,290,235
[45] Date of Patent: Mar. 1, 1994

[54] NON-REUSABLE SYRINGE

[75] Inventors: Alan H. Polyblank, 1/401 New South Head Road, Double Bay, NWS 2028, Australia; Alexander S. Richardson, West Ryde, Australia

[73] Assignee: Alan H. Polyblank, Double Bay, Australia

[21] Appl. No.: 924,947

[22] Filed: Aug. 5, 1992

[30] Foreign Application Priority Data

Feb. 15, 1990 [AU] Australia .................. PJ8666
Dec. 10, 1990 [AU] Australia .................. PK3819
Aug. 5, 1991 [AU] Australia .................. PK7588

[51] Int. Cl.$^5$ .............................................. A61M 5/00
[52] U.S. Cl. ........................................ 604/110; 604/218
[58] Field of Search ............... 604/110, 187, 218, 220

[56] References Cited

U.S. PATENT DOCUMENTS 4,731,068  3/1988  Hesse .................... 604/110

FOREIGN PATENT DOCUMENTS

| 5877990 | 1/1991 | Australia . | |
| 0360329 | 3/1990 | European Pat. Off. | A61M 5/50 |
| 0376697 | 7/1990 | European Pat. Off. | A61M 5/50 |
| 2181580 | 12/1973 | France | A61M 5/00 |
| 8802640 | 4/1988 | PCT Int'l Appl. . | |
| 8904187 | 5/1989 | PCT Int'l Appl. . | |
| 9004424 | 5/1990 | PCT Int'l Appl. . | |
| 9112039 | 8/1991 | PCT Int'l Appl. . | |
| 2220143 | 1/1990 | United Kingdom | A61M 5/315 |

Primary Examiner—John D. Yasko
Attorney, Agent, or Firm—Rothwell, Figg, Ernst & Kurz

[57] ABSTRACT

A syringe device (10) which is not reusable after the first delivery stroke. The syringe has a hollow body (11) slidably containing a plunger (12) in fluid sealing relationship. The plunger (12) has a plunger rod (13) which includes a guide arrangement (17) receiving and guiding a locking member (18). The guide arrangement (17) is adapted to maintain the locking member (18) in an unengaged position relative to the body (11) when the plunger (12) is moved in the direction of a first intake stroke and in a first delivery stroke, and allows relative sliding movement and consequential pivoting movement of the locking member (18) such that, upon commencement of a second intake stroke, the locking member (18) snaggingly engages the inside surface of the body (11) to resist further movement of the plunger (12) in the intake stroke direction. Accordingly, in use, the locking member (18) interacts with the guide arrangement (17) of the plunger (12) and the inside surface of the body (11) so as to allow a first intake stroke and a delivery stroke, but to prevent a second intake stroke of the plunger (12). The syringe device (10) may also allow for aspiration testing, and may have a plunger rod (113) which has two interacting parts (113A, 113B).

11 Claims, 13 Drawing Sheets

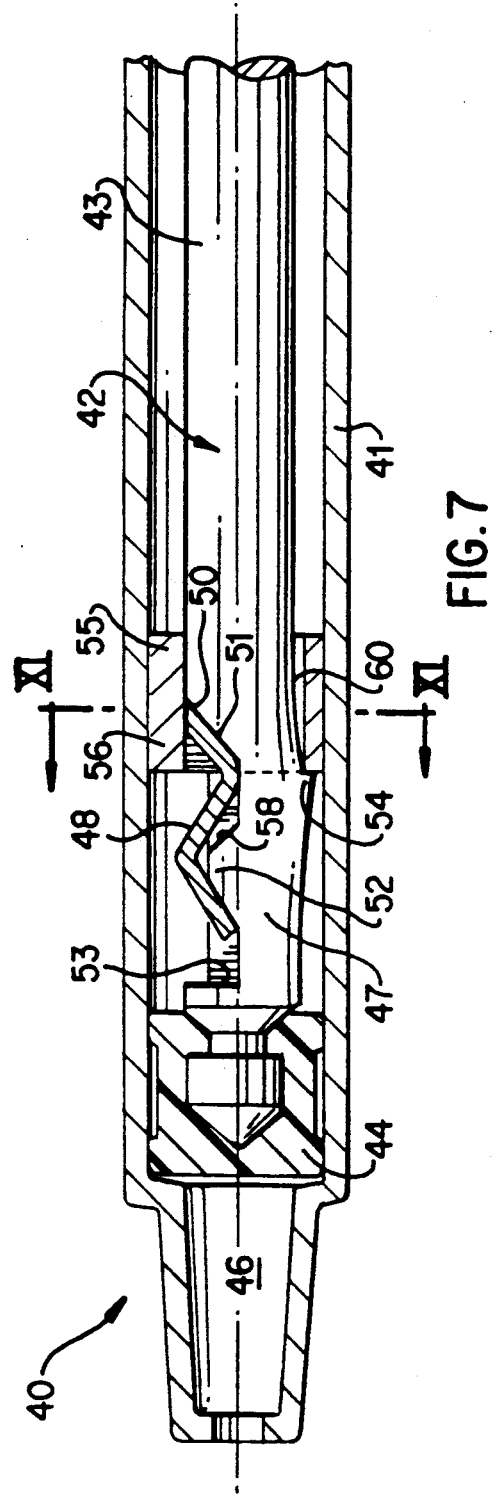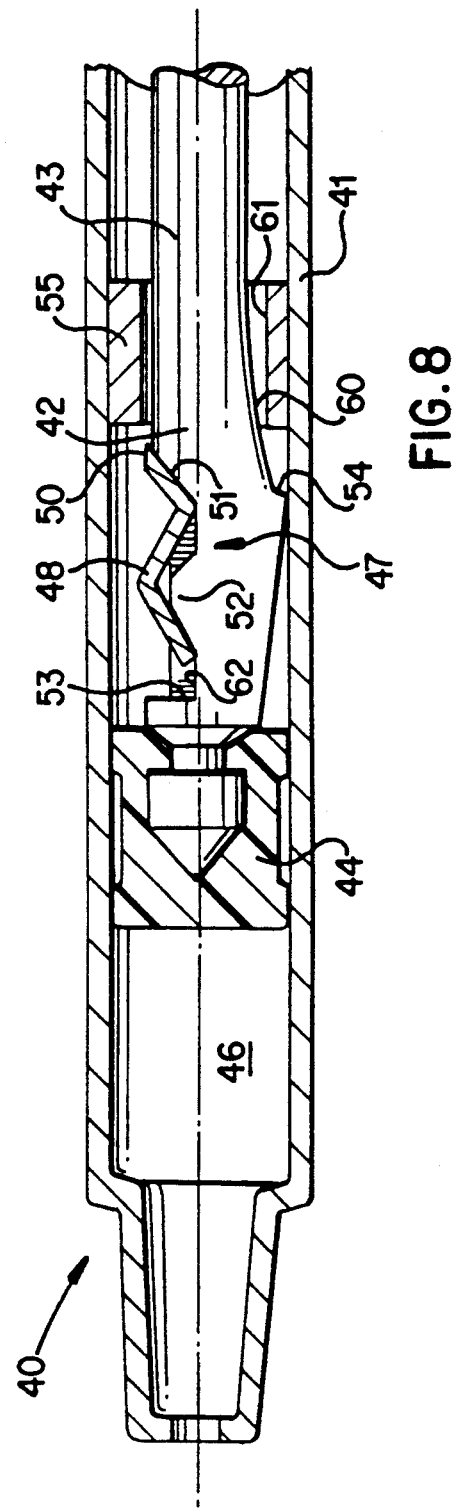

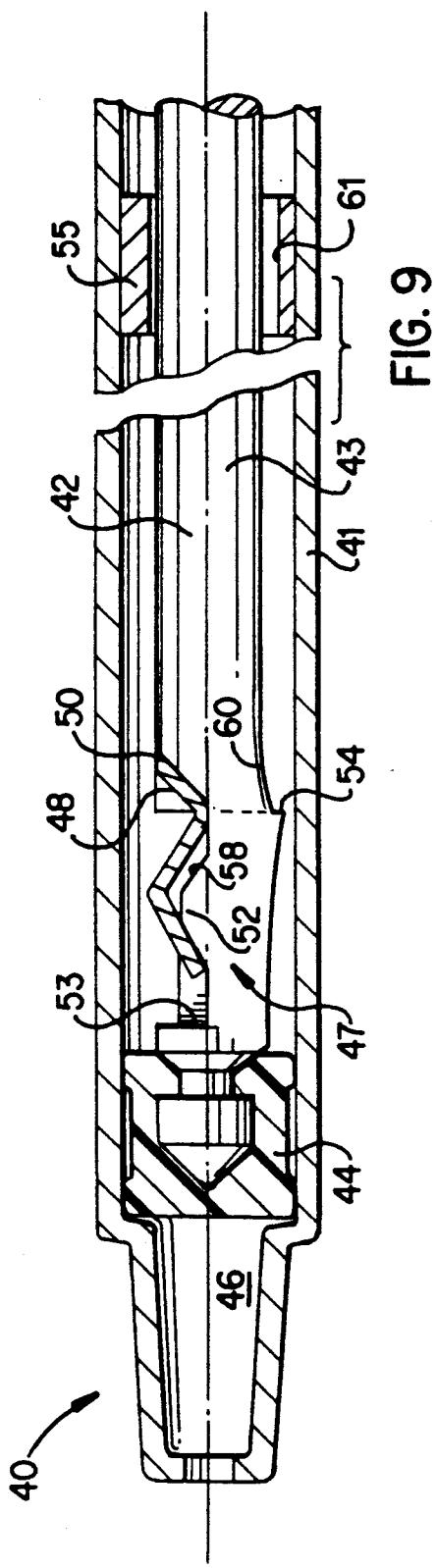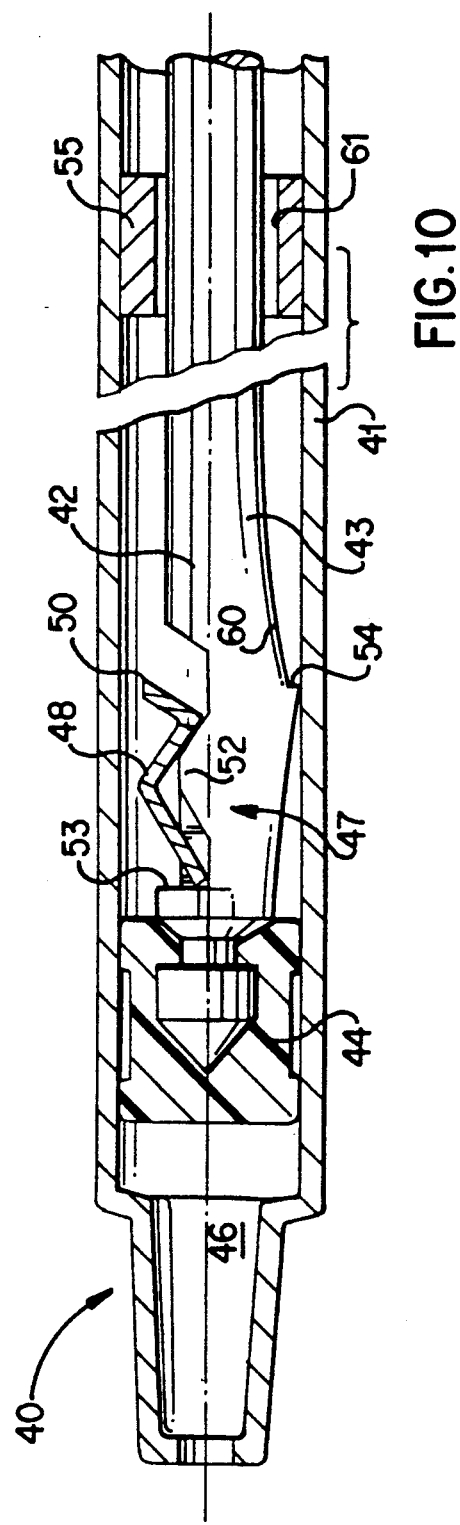

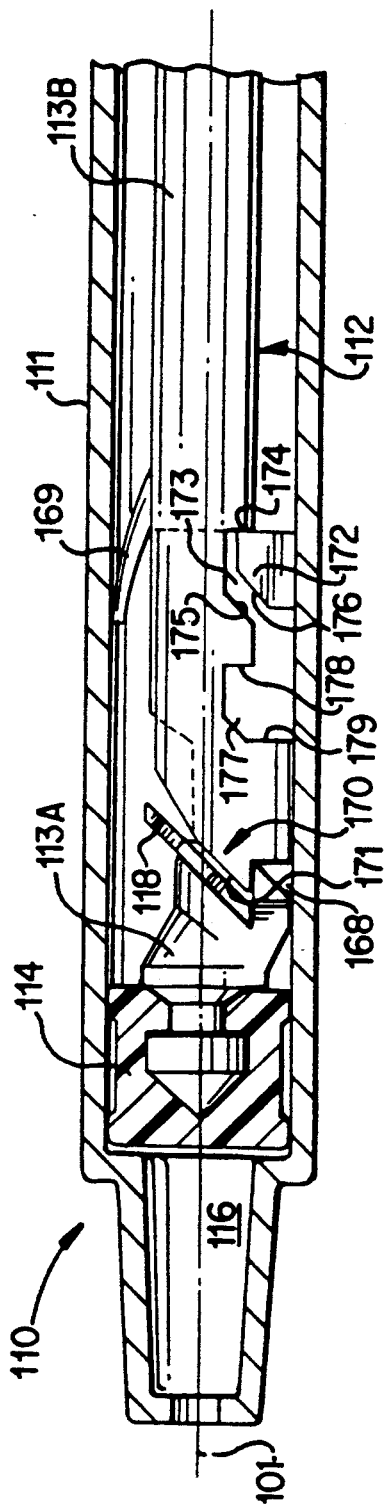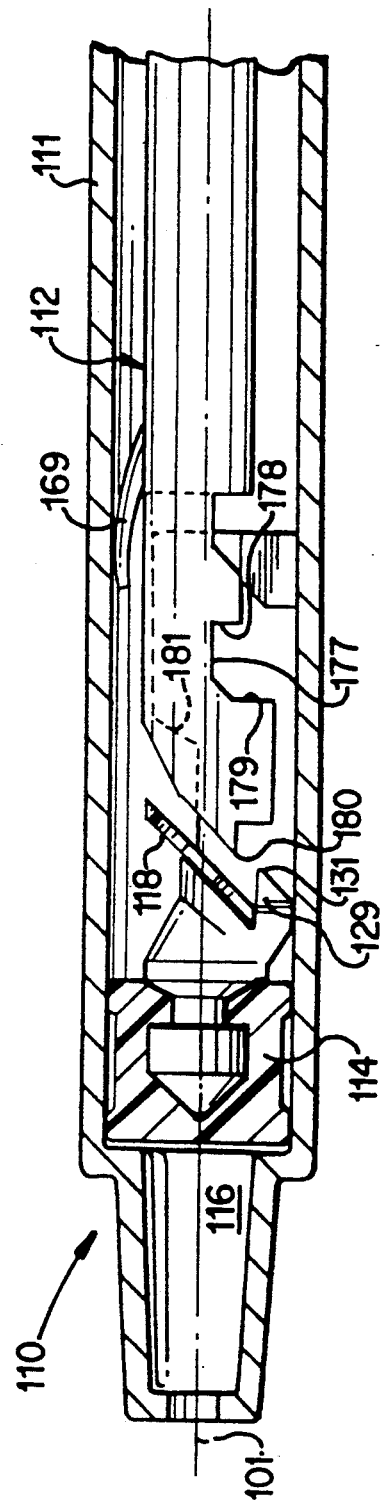
FIG. 12
FIG. 13

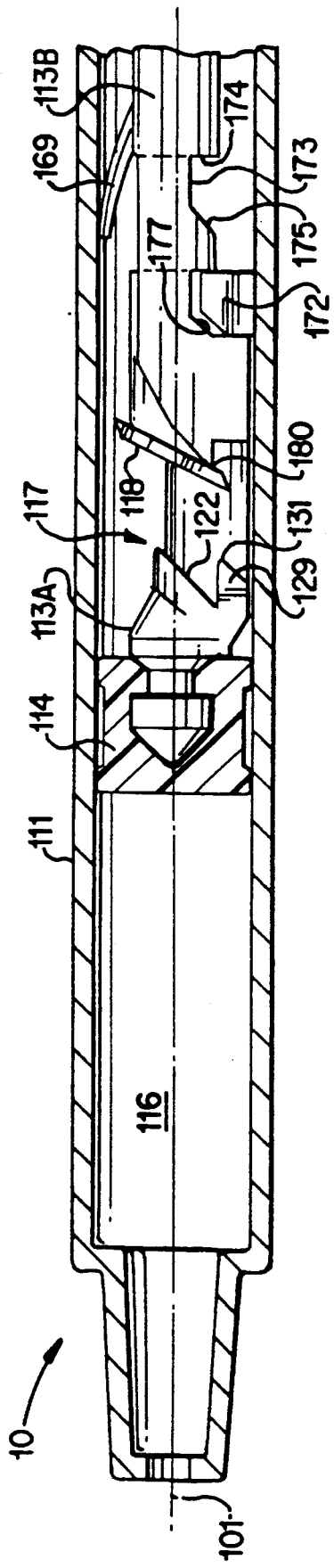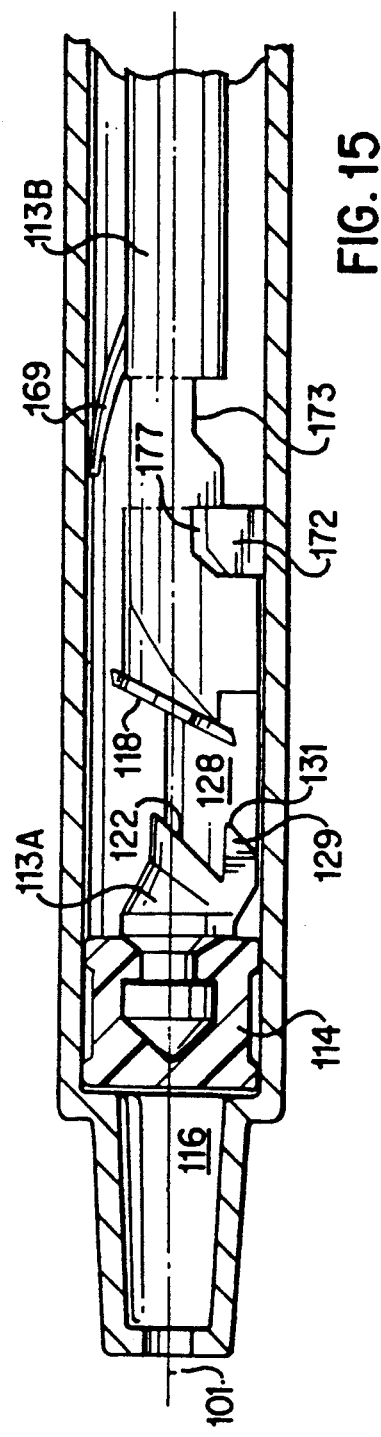

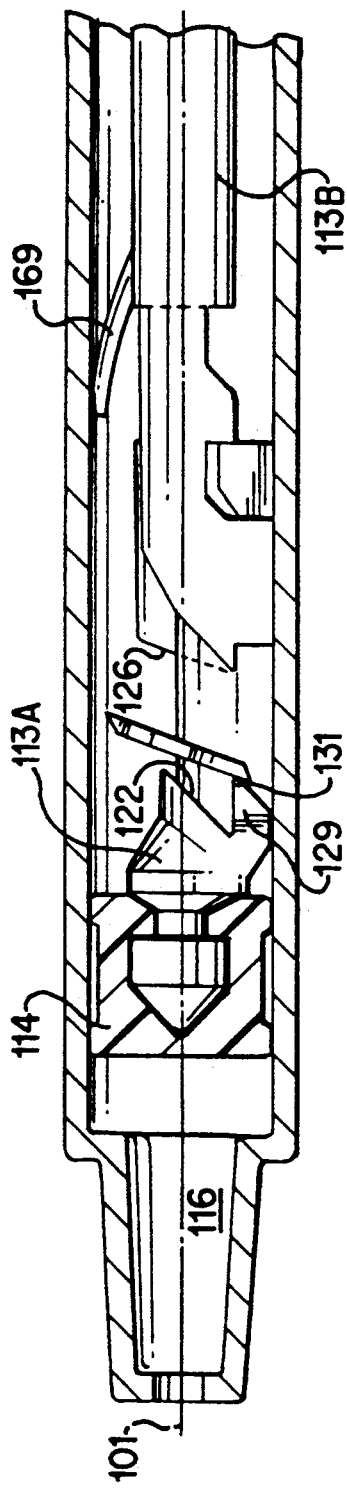
FIG. 16
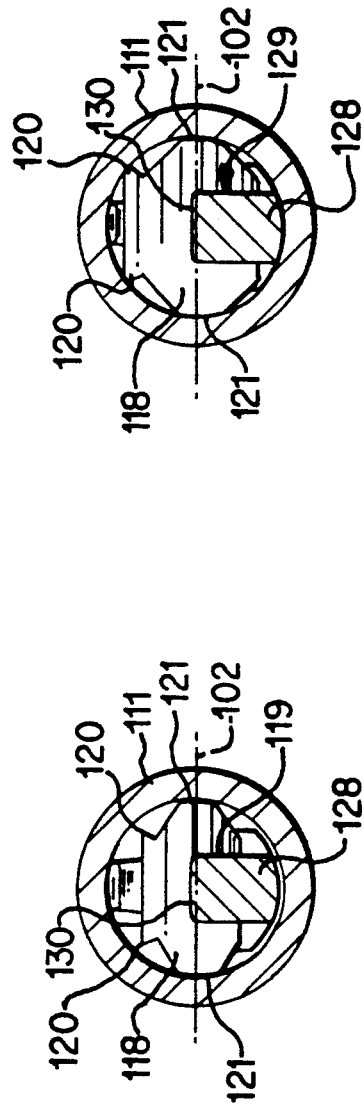
FIG. 17
FIG. 18

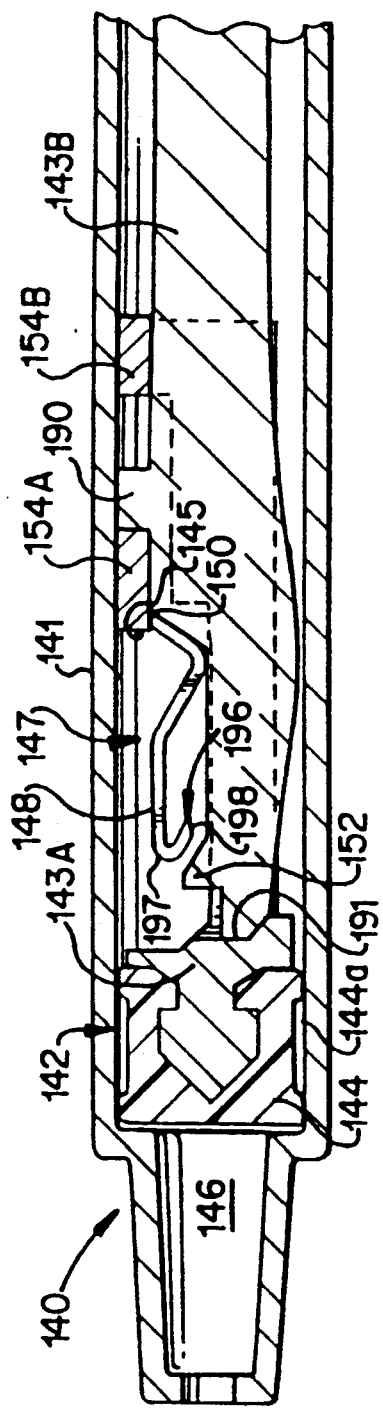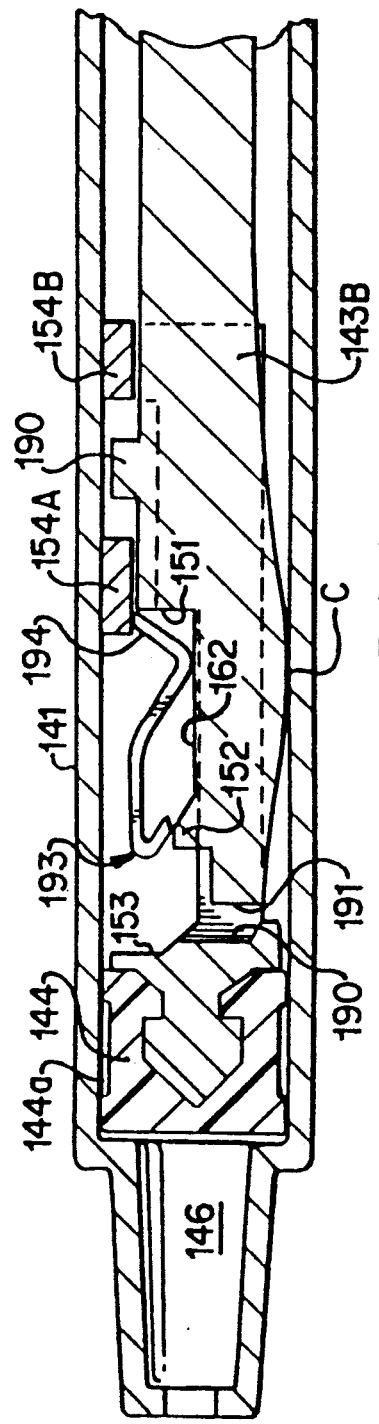

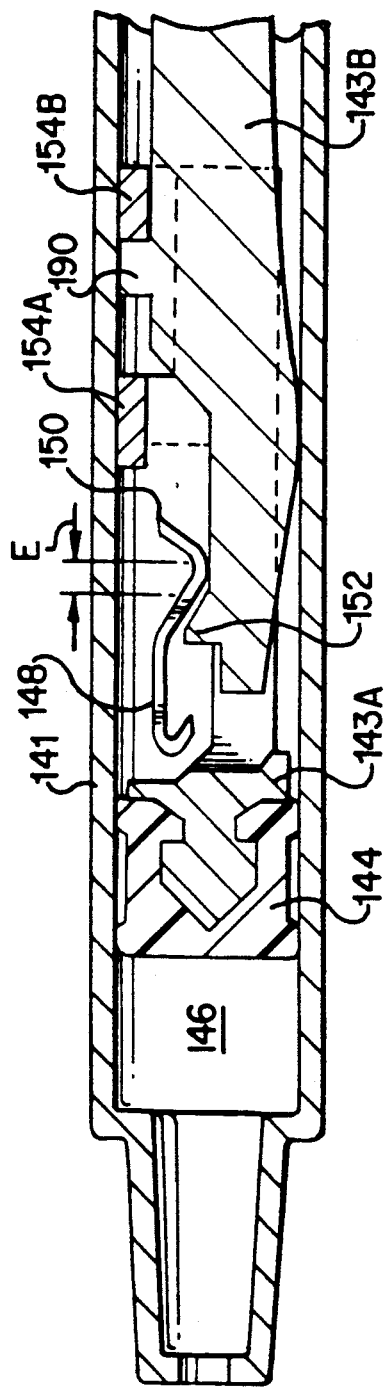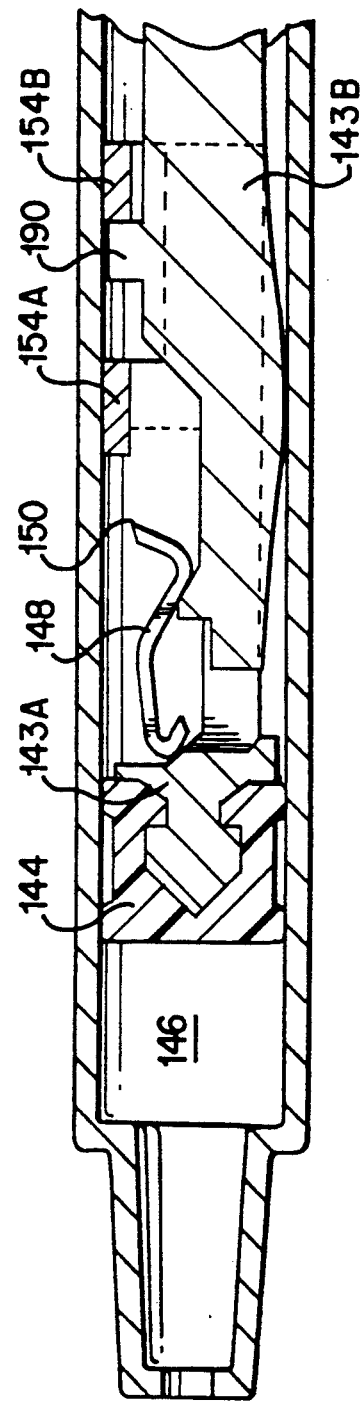

NON-REUSABLE SYRINGE

CROSS-REFERENCE TO RELATED APPLICATIONS

This application is a continuation-in-part of copending International Application No. PCT/AU91/00054, filed Feb. 15, 1991, in which the United States has been designated and elected.

1. Field of Invention

The present invention relates to a non-reusable syringe, and more particularly to an improved syringe construction which prevents re-use and is convenient to manufacture.

2. Description of Prior Art

It is well known in the art to provide a syringe having a substantially cylindrical hollow body with one end open to receive a plunger and piston arrangement, and the other end adapted to receive a hypodermic needle, cannular or the like. In such syringes, the plunger and piston are normally formed as one piece and act in sealing relationship with the inside surface of the syringe body. When a medicament or the like is to be drawn into a syringe of this known type, the plunger and piston arrangement is withdrawn in an intake stroke, and to expel the medicament the plunger and piston arrangement is moved in a delivery stroke back towards the other end of the syringe body so that the medicament is delivered via the hypodermic needle or cannular into the desired place such as a vein, organ etc.

It is nowadays desirable to prevent reuse of a syringe in certain circumstances so as to prevent communicating highly infectious diseases. The heretofore known syringes have the disadvantage that they may be refilled by subsequent withdrawal of the plunger and piston arrangement by the user, or, by pressure within a vial into which the needle of the syringe is inserted.

There have been many attempts to provide a syringe which is designed to prevent a second intake stroke and thereby render the syringe useless after the first delivery stroke. Most of the prior art devices have required a sleeve member or the like which cooperates with the plunger at least during a first intake stroke, and which prevents its operation when a second intake stroke is attempted. Although such devices can work effectively, it would be desirable, for example, to eliminate the need for the sleeve member and thereby simplify the locking mechanism. The construction of the device could also be simplified and may reduce the manufacturing cost of the syringe. Further, the syringe should preferably be able to be operated in the same manner as heretofore known syringes, and should allow techniques such as aspiration testing which allows the user to ensure, depending on what is being injected and where, that he has, or has not, found a vein or artery.

SUMMARY OF THE INVENTION

One broad form of the present invention provides a syringe device comprising:
- a generally elongate hollow body slidably containing a plunger end of a plunger in fluid sealing relationship therewith, the hollow body having a first end having a fluid inlet/outlet, and a second end opposite to the first end;
- the plunger further comprising an elongate plunger rod attached at one end thereof to the plunger end with the other end of the plunger rod projecting out from the second end of the hollow body for slidably moving the plunger end along and within the hollow body;
- wherein the plunger rod comprises a guide means which extends along the plunger rod, and which receives and is adapted to gude a locking member which has at least one snag projection facing in a direction away from the first end of the body and towards the inside surface of the body;
- and wherein, in use, the guide means functions to maintain the locking member in an unengaged position wherein the snag projection is spaced from an inside surface of the body when the plunger is moved in the direction of a first intake stroke away from the first end of the body and in a first delivery stroke towards the first end of the body, and allows relative sliding movement and causes relative pivoting movement of the locking member with respect to the guide means such that, upon commencement of a second intake stroke, the locking member snaggingly engages the inside surface of the body to resist further movement of the plunger in the intake stroke direction.

Preferably, the locking member has one or more portions which are in frictional sliding engagement with the inside surface of the body.

Preferably, the guide means has a first stop means against which the locking member bears during the first intake stroke, a second stop means spaced from said first stop means and against which the locking member bears during the delivery stroke, and a slide means extending between the first and second stop means along which the locking member slides during use of the syringe device.

Furthermore, it is preferable that the first stop means causes the locking member to be orientated at a first angle with respect to a longitudinal axis of the plunger rod during the first intake stroke, the second stop means causes the locking member to be orientated at a second angle with respect to the longitudinal axis which is greater than said first angle, and wherein the guide means has an interference portion which causes the locking member to pivot further away from the longitudinal axis and thereby snaggingly engage the inside surface of the hollow body when a second intake stroke is started. Preferably the interference portion is spaced from the second stop means so as to allow for aspiration testing of the syringe device.

Alternatively, in the above defined broad form of the invention, the guide means may comprise:
- a sleeve member which retains the locking member adjacent a first stop means during the first intake stroke, with the locking member bearing against the first stop means during the delivery stroke;
- a sliding means which has a contoured portion along which the locking member slides and is caused to snaggingly engage the inside surface of the body during the second intake stroke; and
- a second stop face against which the locking member bears when snaggingly engaged with the inside surface for preventing the further movement of the plunger in the intake stroke direction.

Preferably, the sleeve member is caused to move in unison with the plunger and to retain the locking member during the first intake stroke, and wherein the sleeve member is caused, due to its frictional engagement with the inside surface of the body, to move along the plunger and release the locking member when the plunger is moved in a delivery stroke. Preferably, the guide means allows for a predetermined amount of movement in the second intake stroke direction before the locking member snaggingly engages the inside surface of the body for aspiration testing of the syringe device.

In another more preferred form, the plunger rod is formed by two or more members which cooperate and, in combination, define the guide means for receiving and guiding the locking member.

Preferably the interference portion is located between the first and second stop means and is spaced a predetermined distance from the second stop means so as to allow for aspiration testing of the syringe device without causing the locking member to pivot and snaggingly engage the inside surface of the hollow body.

BRIEF DESCRIPTION OF THE DRAWINGS

Preferred forms of the present invention will now be described by way of example with reference to the accompanying drawings, wherein:

FIG. 7 is a longitudinal sectional view of the syringe of a second embodiment of the present invention with the plunger in the ready-for-intake position;

FIG. 8 is a longitudinal sectional view of the syringe of FIG. 7 during the delivery stroke;

FIG. 9 is a longitudinal sectional view of the syringe of FIGS. 7 or 8 when the plunger has been returned to the ready-for-intake position after the delivery stroke;

FIG. 10 is a longitudinal sectional view of the syringe of FIGS. 7, 8 or 9 where a second intake stroke of the plunger has been started.

FIG. 12 is a longitudinal-sectional view of the syringe of a first embodiment of the present invention with the plunger in the ready-for-intake position after assembly;

FIG. 13 is a longitudinal-sectional view of the syringe of FIG. 12 during the initial stage of the intake stroke;

FIG. 14 is a longitudinal-sectional view of the syringe of FIGS. 12 or 13 when the plunger has been moved so as to complete the intake stroke and has been moved a short distance in the delivery stroke;

FIG. 15 is a longitudinal sectional view of the syringe of FIGS. 12 to 14 at the end of the delivery stroke;

FIG. 16 is a longitudinal-sectional view of the syringe of FIGS. 12 to 15 where a second intake stroke of the plunger has been started;

FIG. 17 is a cross-sectional view of the syringe of FIG. 12;

FIG. 18 is a cross sectional view of the syringe of FIG. 16;

FIG. 19 is a longitudinal sectional view of the syringe of a second embodiment of the present invention with the plunger in the ready-for-intake position;

FIGS. 20 and 21 are longitudinal sectional views of the syringe of FIG. 19 during the initial stage of the intake stroke;

FIG. 23 and 24 are longitudinal sectional views of the syringe of FIGS. 19 to 22 where a second intake stroke of the plunger has been started.

PREFERRED EMBODIMENTS OF THE INVENTION

Figure 1:
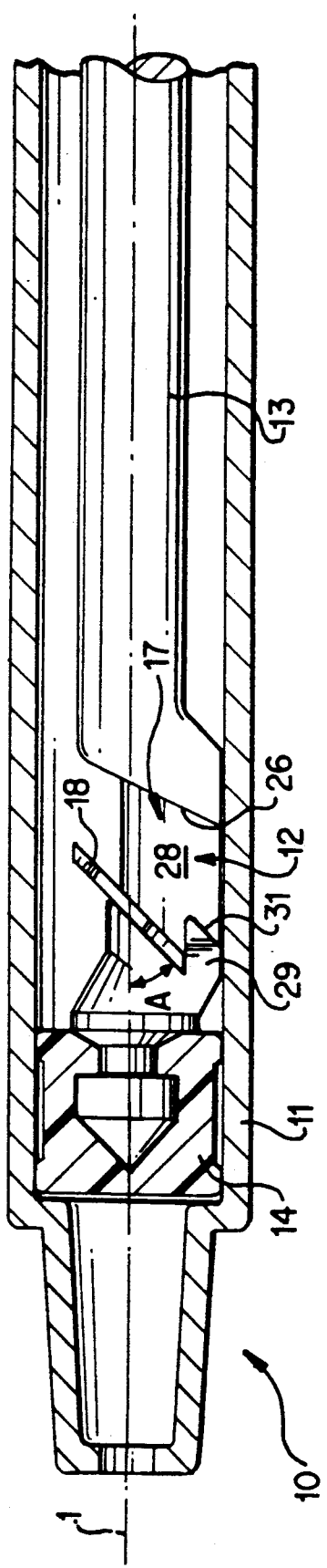
FIG. 1 is a longitudinal-sectional view of the syringe of a first embodiment of the present invention with the plunger in the ready-for-intake position.
Figure 2:
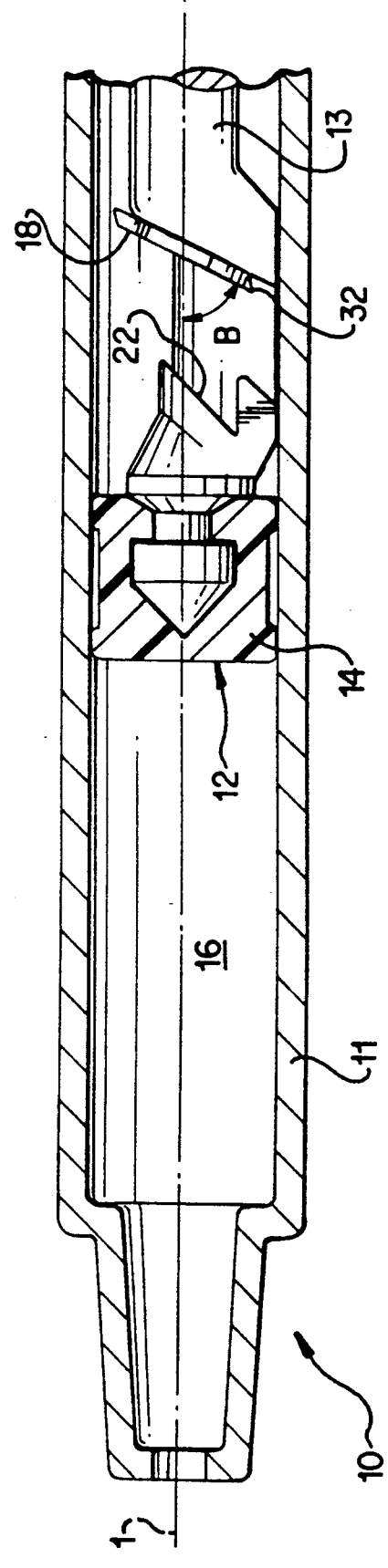
FIG. 2 is a longitudinal-sectional view of the syringe of FIG. 1 during the delivery stroke.
Figure 3:
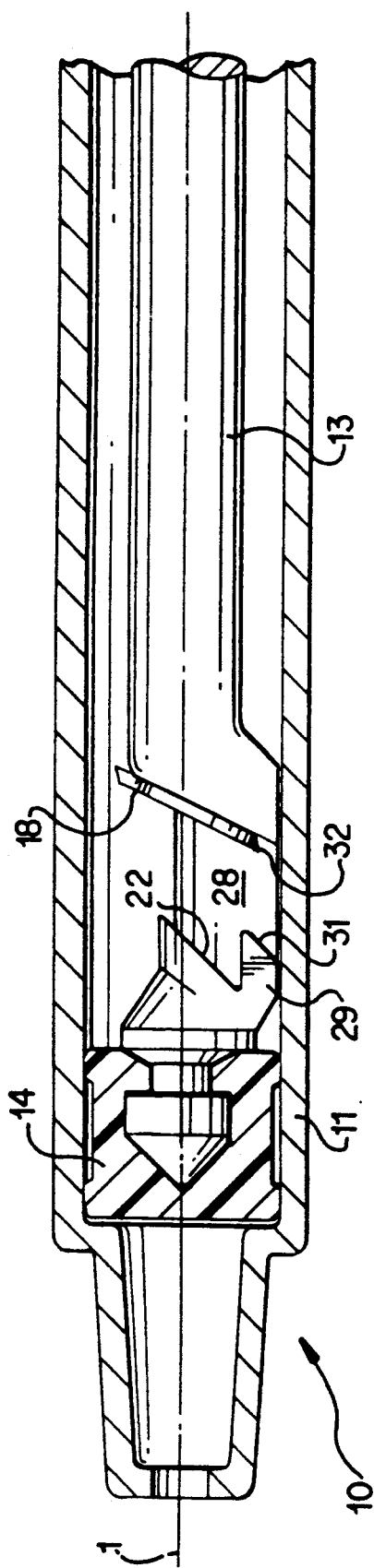
FIG. 3 is a longitudinal-sectional view of the syringe of FIGS. 1 or 2 when the plunger has been returned to the ready-for-intake position after the delivery stroke.
Figure 4:
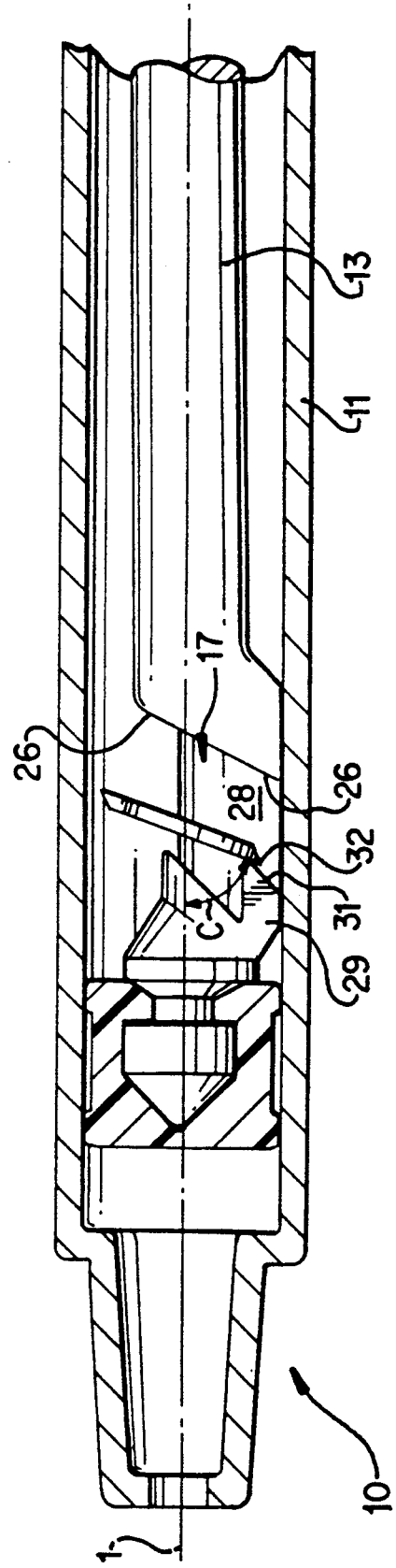
FIG. 4 is a longitudinal-sectional view of the syringe of FIGS. 1, 2 or 3 where a second intake stroke of the plunger has been started.
Figure 5:
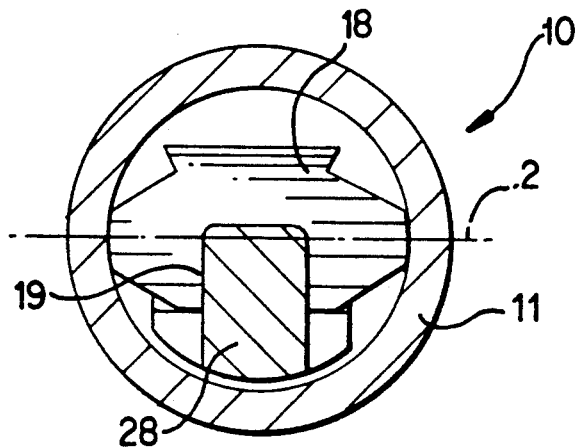
FIG. 5 is a cross-sectional view of the syringe of FIG. 1.
Figure 6:
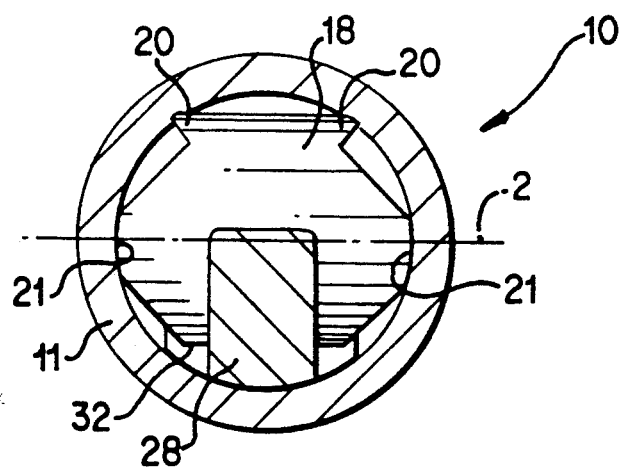
FIG. 6 is a cross sectional view of the syringe of FIG. 4.
Figure 11:
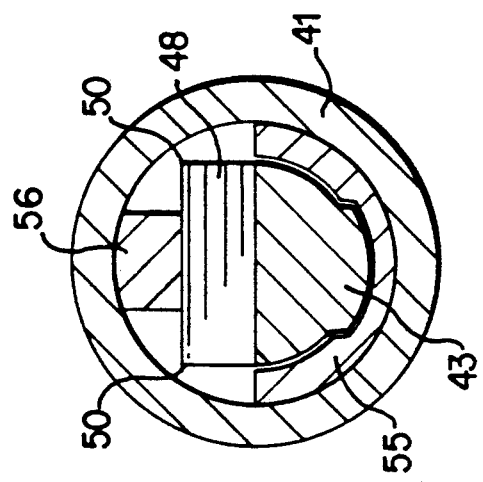
FIG. 11 is a cross-sectional view of the syringe of FIG. 7.

There is shown in the FIGS. 1-6 a first embodiment of the present invention in the form of a syringe 10 comprising a cylindrical body 11, a plunger 12 having a plunger rod 13 and a piston member 14 which is in fluid sealing relationship with the inside surface of the body 11. A needle or cannula or the like (not shown) may be mounted or attached to a forward end of the body 11, and which fluidly communicates with the space 16 defined by the internal recess of the body 11 and the piston member 14.

The piston member 14 and the plunger shaft 13 may be separate pieces secured together on assembly of the syringe 10, or alternatively may be a single integral member. The needle may be permanently attached to the body 11 or may be detachable therewith.

The plunger rod 13 is specially formed to provide a guide arrangement 17 for a locking member 18 which is movably mounted in the guide arrangement 17.

The locking member 18 is generally planar with a lower central recess 19, upper snag projections 20 and side edges 21.

The guide arrangement 17 comprises a first stop face 22 at the piston end of the guide arrangement 17, a second stop face 26 at the opposite end 27 of the guide arrangement 17, and a guide rail 28 extending between the two faces 22, 26. There is also provided a step 29 extending from the first stop face 22, generally parallel to, and below the upper surface of the guide rail 28. The end face 31 of the step 29 is located between the two stop faces 22, 26 in the longitudinal direction of the plunger shaft 13, and extends transversally downwards with respect to the longitudinal axis 1 of the plunger rod 13.

The first stop face 22 extends at a first angle 'A' with respect to the axis 1, and the second stop face 26 extends at a second angle 'B' with respect to the axis 1.

The recess 19 of the locking member 18 receives the guide rail 28, and the upper edge 30 of the recess 19 is caused to rest on the rail 28. The side edges 21 are curved and are in frictional contact with the inside surface of the cylinder 11. This arrangement allows the locking member 18 to pivot about an axis 2 generally normal to the longitudinal axis 1 of the plunger rod 13

The angle 'A' of the first stop face 22 is less than the angle 'B' of the second stop face 26. The locking member 18 is configured such that at a predetermined snag angle 'C', the snag projections 20 snaggingly engage the inside surface of the cylinder 11. The snag angle 'C' is greater than angle 'B'.

The locking member 18 is movable in the guide arrangement 17 between a first unengaged position adjacent the first stop face 22 (refer FIG. 1), a second unengaged position adjacent the second stop face 26 (refer FIG. 2) and a third engaged position when the end face 31 of the step 29 engages the bottom edges 32 of the locking member 18 when a second intake stroke is attempted. (Refer FIG. 4).

For the syringe 10 to be useful as a non-reusable device, it is essential that the plunger cannot be fully withdrawn and separated from the cylinder 11 as this would allow removal of the locking member 18. Accordingly, there is provided stops (not shown) which prevent full withdrawal of the plunger 12 from the cylinder 11. These stops are formed after insertion of the plunger 12.

In use, the syringe 10 is assembled such that the plunger 12 is in the ready-for-intake position and the locking member 18 is positioned adjacent the first stop face 22. In this position, the bottom edges 32 of the locking member 18 are adjacent the step 29, the curved side edges 21 of the locking member contact the inside surface of the cylinder 11, and the locking member 18 lies generally parallel to the first stop face 22. In this first position, the snag projections 20 are spaced from the inside surface of the cylinder 11. The locking member 18 retains this position relative to the guide arrangements 17 during the first intake stroke.

When the plunger 12 is moved in a delivery stroke back towards ready-for-intake position, the locking member 18 slides along the guide rail 28 by virtue of its frictional engagement with the inside surface of the cylinder 11, and retains its orientation (i.e. angle 'A') with respect to the plunger axis 1 until it hits the second stop face 26. When it reaches the second stop face 26, the locking member 18 is caused to pivot and lie against the second stop face 26 at the second orientation angle 'B'. In this position, the snag projections 20 are still spaced from the inside surface of the cylinder 11, but the bottom edges 32 of the locking member 18 are now spaced, in the same radial direction further from the axis 1 than is the step 29.

When the plunger 12 is moved in a second intake stroke back towards the ready-for-delivery position, a short movement of the plunger 12 brings the end face 31 of the step 29 into engagement with the bottom edges 32 of the locking member 18, which causes further pivotal movement of the locking member 18 about its pivot axis 2, and which brings the snag projections 20 into snagging engagement with the inside surface of the cylinder 11 thereby preventing further movement of the plunger 12 with respect to the cylinder 11. That is, the locking member 18, when it engages the inside surface of the cylinder 11, is caused to bear against the top of the rail guide 28 which forces the plunger 13 to also bear against the inside surface of the cylinder 11 opposite the snag projections 20. When the snag projections 20 engage the inside surface of the cylinder 11, this renders the syringe 10 useless. That is, any further force applied to move the plunger 12 in the second intake stroke is translated into a moment force on the locking member 18 which in turn causes the snag projections 20 to bear more forcefully against the inside surface of the cylinder 11.

This arrangement allows for normal techniques generally employed during the use of a syringe as, for example, a hypodermic device. That is, medical staff, when using the syringe as a hypodermic device, first intake a medicament through the needle by withdrawing the plunger 12 from the cylinder 11 in the first intake stroke. Alternatively, the needle is inserted into a pressurized source of medicament which in turn pressurizes the space 16 of the cylinder 11 and forces the plunger 12 to withdraw in an intake stroke. When the desired dosage of medicament is within the space 16 of the syringe 10, the user may then remove any air from the syringe 10 by holding the needle end upwards, tapping the syringe to cause the air to move towards the needle and pushing the plunger 12 a short distance (i.e. a short delivery stroke) to expel the air. The person may then insert the needle hypodermically into a vein or tissue of the patient depending on what is being injected. To test whether the needle is in fact located within a vein or, alternatively, is not in a vein or an artery, the user may withdraw the plunger a short distance enough to sight blood in the syringe 10 (i.e. a short intake stroke) commonly called aspiration testing. The medicament would then be delivered into the desired location by pushing the plunger 13 in a delivery stroke.

The fact that the locking member 18, in the initial movement of the plunger 13 in the first delivery stroke, may generally retain its first orientation angle 'A' before it hits the second stop face 26, allows for such techniques and specifically the combination of removing the air from the syringe followed by aspiration testing.

That is, a short delivery stroke for removing any air from the syringe 10 will move the locking member 18 away from the first stop face 22 to a position near or against the second stop face 26. Aspiration testing will then cause relative 10 movement of the locking member 18 away from the second stop 26 with the guide means allowing relative movement at least back to the front face 31 of the step 29, and if the locking member remains in the first orientation angle 'A', may also allow movement back to the first stop face 22 15 without the step 29 causing the locking member 18 to rotate and snaggingly engage the inside surface of the cylinder. The distance 'x' between the second stop face 26 and the front face 31 of the step 29 will normally be greater than the length of the short intake stroke for aspiration testing. Accordingly, even if the locking member 18 hits the second stop face 26 and pivots into the second orientation angle 'B' when air is expelled during a short delivery stroke, the distance 'x' will be greater than the relative movement of the locking member during aspiration testing.

There is shown in FIGS. 7–11 a second embodiment of the present invention in the form of a syringe 40 comprising a cylindrical body 41, a plunger 42 having a plunger rod 43 and a piston member 44 which is in fluid sealing relationship with the inside surface of the body 41. A needle or cannular or the like (not shown) may be mounted or attached to a forward end of body 41 and which fluidly communicates with the space 46 defined by the internal recess of the body 41 and the piston member 44.

The piston member 44 and the plunger rod 43 may be separate pieces secured together on assembly of the syringe 40, or alternatively may be a single integral member. The needle or mounting arrangement for the cannular may be permanently attached to the body 41 or may be detachable therewith.

The plunger rod 43 is specially formed to provide a guide arrangement 47 which extends longitudinally of the plunger rod 43. A locking member 48 is movably mounted in the guide arrangement 47.

The locking member 48 has a zig zag shape in the longitudinal section which, in use, cooperates with the guide arrangement 47. The locking member 48 also has snag projections 50 at one end which project transversely away from the longitudinal axis of the plunger 42, and rearwardly of the syringe 40.

The guide arrangement 47 comprises a sliding face 62, a first stop face 51 at one end of the sliding face 62 distal from the piston member 44, a second stop face 53 at the other end of the sliding face 62, and a contoured portion 52 on the sliding face 62 intermediate of the stop faces 51, 53.

The plunger rod 43 further comprises a projection 54 on an opposite side of the guide arrangement 47. The syringe 40 further comprises a sleeve member 55 which is slidably received in the body 41, but which is in frictional contact with the inside surface thereof.

The syringe 40 is assembled such that the plunger 42 is in a ready-for-intake position with the piston member 44 adjacent the forward end of the body 41. In that position, the locking member 48 is in a non-engaged position on the sliding face 62 adjacent the first stop face 51 and straddling the contoured portion 52. The sleeve member 55 is adjacent the projection 54 and has a tab means 56 which bears against the snag projections 50 of the locking member 48 thereby preventing their engagement with the inside surface of the body 41.

In use, the plunger 42 may be withdrawn from the body 41 so as to induct a fluid such as, for example, a medicament into the space 46. During the intake stroke, the sleeve member 55 is caused to remain in the same relative position with respect to the plunger rod 43 by bearing against the projection 54, and the locking member 48 is also caused to remain in the same relative position with respect to the guide arrangement 47 by the tab means 56 on the sleeve member 55.

In this position, the sleeve member 55 keeps the projection 54 of the plunger rod 42 spaced from the inside surface, and also serves to position and align the plunger rod 43 with the longitudinal axis of the body 41 during the first intake stroke.

When the plunger 42 has been withdrawn so as to intake the desired amount of fluid into the space 46, it is then in the ready-for-delivery position. The plunger 42 can then be pushed back into the body 41 in a delivery stroke so as to expel the fluid through the syringe, cannular or the like.

Due to its frictional engagement with the inside surface of the body 41, the sleeve member 55 is caused to remain in the same position relative to the body 41 during the delivery stroke. However, the locking member 48 is caused to remain in the same relative position with respect to the guide arrangement 47 since it bears against the first stop face 51 during the delivery stroke. Accordingly, when the plunger 42 has been moved in the delivery stroke, the locking member 48 moves relative to and away from the sleeve member 55 so as to be released from the tab means 56. When the locking member 48 is sufficiently spaced from the sleeve member 55, the snag projections 50 face the inside surface of the body 41.

Further, when the plunger 42 is moved in the delivery stroke, the bottom edge 60 of the plunger rod 42, which is slightly curved towards the longitudinal axis of the plunger rod, is spaced from the inside surface 61 of the sleeve member 55 thereby allowing slight misalignment of the longitudinal axis of the plunger rod 42 and the body 41 such that the projection 54 also bears against the inside surface of the body 41.

When the plunger 42 is then moved in a second intake stroke, the locking member 48 will slide along the sliding face 62 a predetermined distance A before riding up the inclined face 58 of the contoured portion 52 whereupon the snag projections 50 will be moved into snagging engagement with the inside surface of the body 41. The locking member 48 bears against the inclined face 58 whilst the projection 54 bears against the inside surface generally opposite from the snag projections 50 thereby preventing further movement of the plunger 42 in the second intake stroke direction.

The guide arrangement 47 is designed to allow the locking member 48 to move therealong the predetermined distance A (defined by the distance between the stop face 50 and the inclined face 58 of the contoured portion 52) during the second intake stroke before the locking member 48 engages the inside surface. This allows the user to perform aspiration testing to ensure, for example, that the needle is/is not within a vain or artery.

There is shown in the FIGS. 12-17 a third embodiment of the present invention in the form of a syringe 110 comprising a cylindrical body 111, a plunger 112 having a plunger rod 113 and a piston member 114 which is in fluid sealing relationship with the inside surface of the body 111. A needle or cannula or the like (not shown) may be mounted or attached to a forward end of the body 111, and which fluidly communicates with the space 16 defined by the internal recess of the body 111 and the piston member 114.

The needle may be permanently attached to the body 111 or may be detachable therewith.

The plunger rod 113 is specially formed in two pieces 113A, 113B and provides a guide arrangement 117 for a locking member 118 which is movably mounted in the guide arrangement 117.

That is, the plunger rod 113 comprises a first part 113A and a second part 113B. The first part 113A, which defines a first stop face 122, a guide rail 128 and a second stop face 126 of the guide arrangement 117, and the second part 113B are movable with respect to each other between a retracted position wherein the locking member 118 is retained in a first unengaged position with respect to the inside surface of the body, and a second extended position spaced from the guide means 117.

The locking member 118 is generally planar with a lower central recess 119, upper snag projections 120 and side edges 121.

The guide arrangement 117 comprises the first stop face 122 at the piston end of the guide arrangement 117, the second stop face 126 at the opposite end 127 of the guide arrangement 117, and the guide rail 128 which extends between the two stop faces 122, 126. There is also provided a step 129 extending from the first stop face 122, generally parallel to, and a predetermined distance below the upper surface of the guide rail 128. The end face 131 of the step 129 is located between the two stop faces 122, 126 in the longitudinal direction of the plunger rod 113, and extends transversely downwards with respect to the longitudinal axis 101 of the plunger rod 113.

The first stop face 122 extends at a first angle 'A' with respect to the axis 101, and the second stop face 126 extends at a second angle 'B' with respect to the axis 101.

The recess 119 of the locking member 118 receives the guide rail 128, and the upper edge 130 of the recess 119 is caused to rest on the rail 128 and defines the pivot axis of the locking member 118. The side edges 121 are curved and are in frictional contact with the inside surface of the cylinder 111. This arrangement allows the locking member 118 to pivot about an axis 102 generally normal to the longitudinal axis 101 of the plunger rod 113.

The angle 'A' of the first stop face 122 is less than the angle 'B' of the second stop face 126. The locking member 118 is configured such that at a predetermined snag angle 'C', the snag projections 120 snaggingly engage the inside surface of the cylinder 111. The snag angle 'C' is greater than angle 'B'.

When the plunger rod 113 is in the extended position, the locking member 118 is movable in the guide arrangement 117 between a first unengaged position adjacent the first stop face 122 (refer FIG. 13), a second unengaged position adjacent the second stop face 126 (refer FIG. 14) and a third engaged position when the end face 131 of the step 129 engages the bottom edges 132 of the locking member 118 when a second intake stroke is attempted. (Refer FIG. 16).

The two parts 113A and 113B of the plunger rod 113 cooperate as follows. The forward end 170 of the second part 113B is shaped such that it has a face 171 which extends generally parallel with the first stop face 122 of the guide means 117, and a recess 168 which receives the step 129, such that the face 171 can be spaced a short distance from the first stop face 122 with the locking member 113 positioned therebetween in the retracted position of the plunger rod 113. In this retracted position, the locking member 118 is retained in its first unengaged position. The two parts 113A and 113B are slidably movable with respect to each other from the retracted position to an extended position wherein the forward end 170 of the second part does not intrude in the cooperation of the locking member 118 in the guide means 117. The parts 113A and 113B can be moved from the retracted position to the extended position by pulling the second part 113B in a direction away from the first member 113A. In the retracted position, the first part 113A has a lateral projection 172 which is received in a first radially inward recess 173 defined, in the longitudinal direction of the plunger rod 113, by a back stop face 174 and an inclined face 175 spaced from the top face 174.

The projection 172 also has an inclined face 176 which is generally parallel to and faces the inclined face 175 of the second part 113B. This arrangement locates the two parts 113A and 113B in the retracted position. The arrangement, however, allows the two parts 113A and 113B to be moved relative to one another in a sliding manner such that the second part 113B is caused to ride up the inclined face 176 of the projection 172 of the first part 113A.

The second part 113B is also provided with a resilient spring 169 which is resiliently compressed when the second part 113B rides up and over the projection 172 (refer FIG. 13). As the two parts 113A and 113B are moved further apart, the projection 172 will come into alignment with a second radially inward recess 177 of the second part 113B, whereupon the spring 169 causes the second part 113B to move downwards and locate the projection 172 in the second recess 177. The plunger rod 113 is then secured in the extended position. The second recess 177 is defined by a second back stop face 178 and a front stop face 179 which are spaced so as to closely receive the projection 172 (refer FIG. 14).

In the extended position, the leading edge 180 of the second part 113B is generally co-planar with an inclined face 181 of the first part 113A to define, in combination, the second stop face 126 of the guide arrangement 117.

The above described two part plunger rod 113 allows a simple manufacture of the non-reuse syringe. That is, the plunger rod 113 can be assembled in its retracted position with the locking member 118 located in the first unengaged position between the first stop face 122 of the first part 113A, and the forward end face 170 of the second part 113B. In this retracted position, the plunger rod 113 can be simply pushed into the body 111 without requiring, for example, a long probe to keep the locking member in an unengaged position with respect to the inside surface of the body 111. When, during assembly, the plunger rod 113 is being used to push the piston member 114 towards the forward end of the syringe 110, the first back stop face 174 of the second part 113B bears against the projection 172 of the first part 113A. Accordingly, the two parts are retained in the retracted position during this final assembly step.

It is noted that, for the syringe 110 to be useful as a non-reusable device, it is essential that the plunger cannot be fully withdrawn and separated from the cylinder 111 as this would allow removal of the locking member 118. Accordingly, there is provided stops (not shown) which prevent full withdrawal of the plunger 112 from the cylinder 111. These stops are formed after insertion of the plunger 112.

The syringe 110 is then in the ready-for-intake position and the locking member 118 is positioned adjacent the first stop face 122. In this position, the bottom edges 132 of the locking member 118 are adjacent the step 129, the curved side edges 121 of the locking member contact the inside surface of the cylinder 111, and the locking member 118 lies generally parallel to the first stop face 122. In this first position, the snag projections 120 are spaced from the inside surface of the cylinder 111. The locking member 118 retains this position relative to the guide arrangements 117 during the first intake stroke.

However, when the plunger rod 113 is first pulled in the intake stroke direction, the piston member 114 does not immediately move. Rather, the first and second parts 113A, 113B of the piston rod 113 move with respect to each other from the retracted position to the extended position. It is understood that the inherent resistance of the sealing ring of the piston member 114 to move along the inside surface of the body 111 from the ready-for-intake position is sufficient to hold the first part 113A in its initial position relative to the body 111, while the second part 113B is moved away. When the parts 113A, 113B reach the extended position, the front stop face 179 of the second part 113b bears against the projection 172 of the first part 113A such that the first part 113A and the piston member 114 are caused to move in unison with the further movement of the second part 113B during the remainder of the intake stroke.

During the subsequent delivery stroke and any attempted second intake stroke, the plunger rod 113 is retained in the extended position.

When the plunger 112 is moved in a delivery stroke back towards to ready-for-intake position, the locking member 118 slides along the guide rail 128 by virtue of its frictional sliding contact with the inside surface of the cylinder body 111, and generally retains its orientation (i.e. at an angle 'A') with respect to the plunger axis 101 until it hits the second stop face 126. When it reaches the second stop face 126, the locking member 118 is caused to pivot and lie against the second stop face 126 at the second orientation angle 'B'. In this position, the snag projections 120 are still spaced from the inside surface of the cylinder 111, but the bottom edges 132 of the locking member 118 are now spaced, in the same radial direction, further from the axis 101 than is the step 129.

When the plunger 112 is moved in a second intake stroke back towards the ready-for-delivery position, a short movement of the plunger 112 brings the end face 131 of the step 129 into engagement with the bottom edges 132 of the locking member 118, which causes further pivotal movement of the locking member 118 about its pivot axis 102, and which brings the snag projections 120 into snagging engagement with the inside surface of the cylinder 111 thereby preventing further movement of the plunger 112 with respect to the cylinder 111. That is, the locking member 118, when it engages the inside surface of the cylinder 111, is caused to bear against the top of the rail guide 128 which forces the plunger 113 to also bear against the inside surface of the cylinder 111 opposite the snag projections 120. When the snag projections 120 engage the inside surface of the cylinder 111, this renders the syringe 110 useless. That is, any further force applied to move the plunger 112 in the second intake stroke is translated into a moment force on the locking member 118 which in turn causes the snag projections 120 to bear more forcefully against the inside surface of the cylinder 111.

This arrangement allows for normal techniques generally employed during the use of a syringe as, for example, a hypodermic device. That is, medical staff, when using the syringe as a hypodermic device, first intake a medicament through the needle by withdrawing the plunger 112 along the cylinder 111 in the first intake stroke. When the desired dosage of medicament is within the space 116 of the syringe 110, the user may then remove any air from the syringe 110 by holding the needle end upwards, tapping the syringe to cause the air to move towards the needle and pushing the plunger 112 a short distance (i.e. a short delivery stroke) to expel the air. The person may then insert the needle hypodermically into a vein or tissue of the patient depending on what is being injected. To test whether the needle is in fact located within a vein or, alternatively, is not in a vein or an artery, the user may withdraw the plunger a short distance enough to sight blood in the syringe 110 (i.e. a short intake stroke) commonly called aspiration testing. The medicament would then be delivered into the desired location by pushing the plunger 113 in a delivery stroke.

The fact that the locking member 118, in the initial movement of the plunger 113 in the first delivery stroke, may generally retain its first orientation angle 'A' before it hits the second stop face 126, allows for such techniques and specifically the combination of removing the air from the syringe followed by aspiration testing.

That is, a short delivery stroke for removing any air from the syringe 110 will move the locking member 118 away from the first stop face 122 to a position near or against the second stop face 126. Aspiration testing will then cause relative 110 movement of the locking member 118 away from the second stop 126 with the guide means allowing relative movement at least back to the front face 131 of the step 129, and if the locking member remains in the first orientation angle 'A', may also allow movement back to the first stop face 122, 115 without the step 129 causing the locking member 18 to rotate and snaggingly engage the inside surface of the cylinder. The distance 'x' between the second stop face 126 and the front face 131 of the step 129 will normally be greater than the length of the short intake stroke required for aspiration testing. Accordingly, even if the locking member 118 hits the second stop face 126 and pivots into the second orientation angle 'B' when air is expelled during a short delivery stroke, the distance 'x' will be greater than the relative movement of the locking member during aspiration testing.

There is shown in FIGS. 19-25 a fourth embodiment of the present invention showing a syringe 140 comprising a cylindrical body 141, a plunger 142 having a plunger rod 143, and a piston member 144 which has a sealing ring 144a which is in fluid sealing relationship with the inside surface of the body 141. A needle or cannular or the like (not shown) may be mounted or attached to a forward end of body 141, and which fluidly communicates with the space 146 defined by the internal recess of the body 141 and the piston member 144.

The needle or mounting arrangement for the cannular may be permanently attached to the body 141 or may be detachable therewith.

The plunger rod 143 is specially formed in two parts 143A and 143B which cooperate to provide a guide arrangement 147 which extends longitudinally of the plunger rod 143. A locking member 148 is movably mounted in the guide arrangement 147.

The locking member 148 has a zig zag shape in the longitudinal section which, in use, cooperates with the guide arrangement 147. The locking member 148 has snag projections 150 at a rearward end 194 which project transversely away from the longitudinal axis of the plunger 142 (i.e., towards the inside surface of the body 141), and rearwardly of the syringe 140. At the forward end 193 of the locking member 148 there is a hook means 176 in the form of a bent portion 177 with a rearwardly projecting end point 178.

The guide arrangement 147 comprises a sliding face 162, a first end face 151 of the first part 143A at one end of the sliding face 162 which is distal from the piston member 144, a second end face 153 also of the first part 143A at the other end of the sliding face 162, and a contoured portion 152 of the second part 143B positioned on the sliding face 162 intermediate of the end faces 151, 153.

The first part 143A of the plunger rod 143 further comprises two spaced transverse projections 154A and 154B. The second part 143B has a projection 190 which is longitudinally aligned with the projections 154A and 154B, and located therebetween.

Preferably, the first part 143A has two transversely spaced longitudinal legs which slidably receive the forward end of the second part 143B therebetween.

Figure 21:
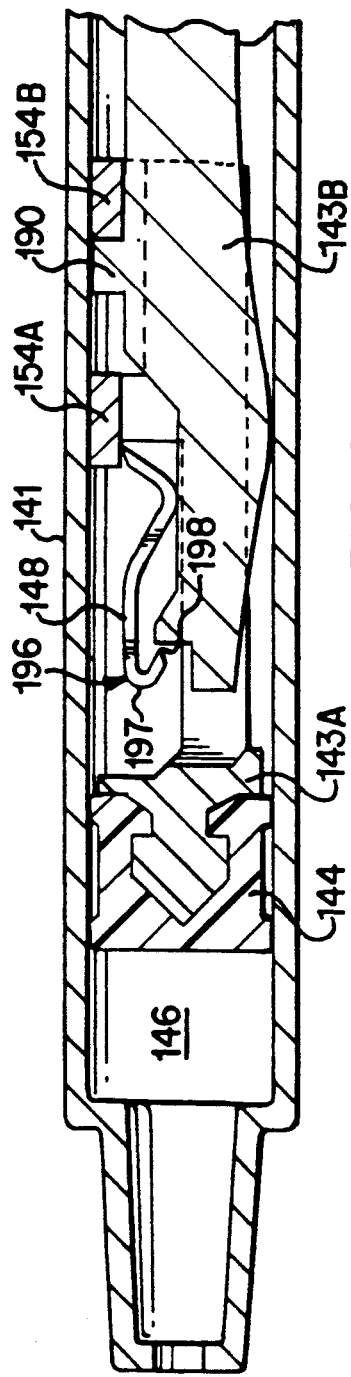
Figure 22:
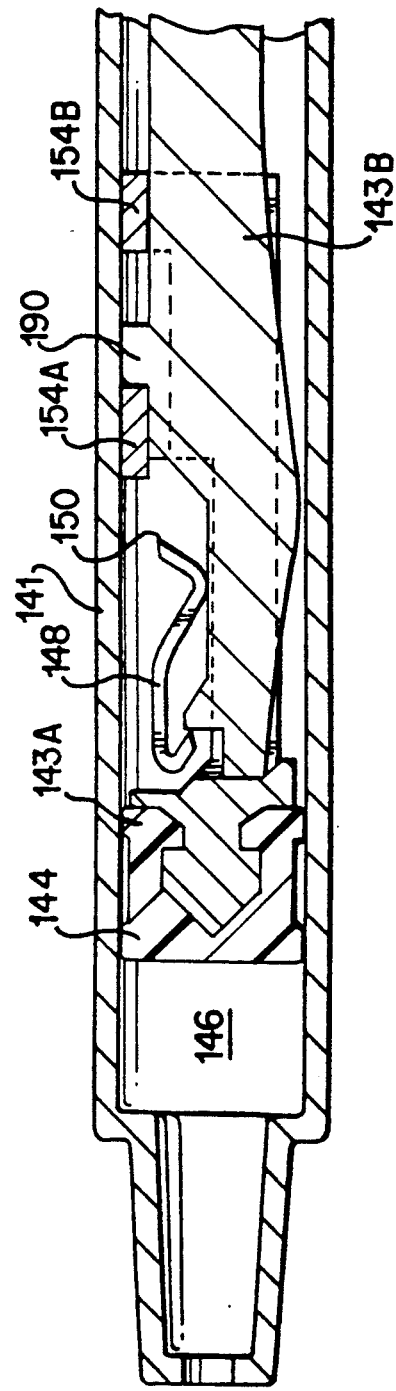
FIG. 22 is a longitudinal sectional view of the syringe of FIGS. 19, 20 and 21 when the plunger is being returned to the ready-for-intake position after the delivery stroke.
Figure 25:
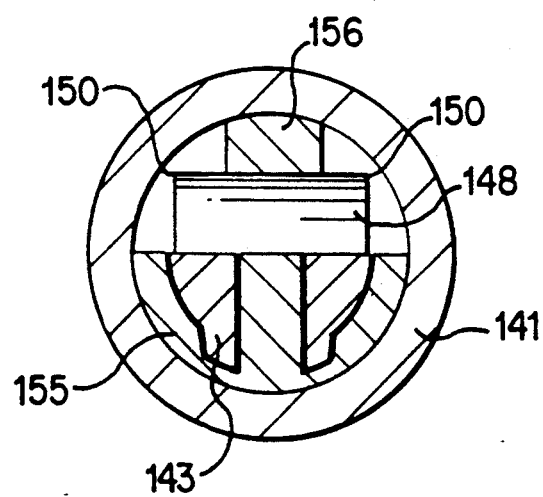
FIG. 25 is a cross-sectional view of the syringe of FIG. 19.

The two parts 143A and 143B of the plunger rod 143 are slidably movable with respect to each other between a retracted position (see FIG. 19) and an extended position (see FIG. 21). In the retracted position, the front end 91 of the second part 143B abuts the stop face 192 of the first part 143A, and the projection 190 of the second part 143B abuts the projection 154A. In this position of the plunger rod 143, the locking member 148 rests on the sliding face 162 defined by both the first part 143A and the second part 143B, with a forward end 193 adjacent the contoured portion 152 and the other end 194 adjacent the first end face 151 and wedged between the overhanging ledge 145 and the sliding face 162. Accordingly, the snag projections 150 on the other end 174 of the locking member 148 are prevented from contacting the inside surface of the body 141 by the overhanging ledge 145 which is defined by the projection 154A of the first part 143A.

The syringe 140 is assembled such that the plunger 142 is in a ready-for-intake position with the piston member 144 adjacent the forward end of the body 141 and the plunger rod 143 in the retracted position (see FIG. 19).

When, in use, the user pulls on the second part 143B of the plunger rod 143, the inherent resistance of the seal ring 144a of the piston member 144 allows for the two parts 143A, 143B to slide with respect to one another and away from the retracted position. In this relative movement of the two parts 143A and 143B, the bent portion 197 of the locking member 148 is caused to ride up and over the contoured portion 152 (see FIGS. 20 and 21) whereby the locking member 148 straddles the contoured portion 152. Continued relative sliding movement of the two parts 143A, 143B is prevented when the projections 190 of the second part 143B comes into abutment with the projection 154B of the first part 143A. Thereafter, the two parts 143A and 143B and the piston member 144 move in unison in the intake stroke direction (see FIG. 21).

The plunger 142 is withdrawn from the body 141 so as to induct a fluid such as, for example, a medicament into the space 146. During the intake stroke, the locking member 148 is caused to remain in the same relative position with respect to the guide arrangement 147 by the overhanging ledge 145 of the first part 143A.

When the plunger 142 has been withdrawn so as to intake the desired amount of fluid into the space 146, it is then in the ready-for-delivery position. The plunger 142 can then be pushed back into the body 141 in a delivery stroke so as to expel the fluid through the syringe, cannular or the like.

During the initial movement of the plunger rod 143 in the delivery stroke direction (i.e. during a delivery stroke or when expelling air from the syringe), the second part 143B slidably moves relative to the first part 143A whereby the contoured portion engages the hook means of the locking member 148 and moves it towards the forward end of the guide arrangement 147 and thereby away from the overhanging ledge until the projection 190 of the second part 143B abuts the projection 154A of the first part 143A (see FIG. 22) whereafter the plunger rod parts 143A and 143B, and the piston member 144 move in unison in the delivery stroke.

When the expelling of air is completed, or when the delivery stroke is completed, the second part 143B is moved in the intake stroke direction slidably away from the first part 143A until the projection 190 abuts the projection 154B, and at which point the inclined face of the contoured portion 152 is spaced a distance "E" from the intermediate inclined portion of the locking member 148. This distance "E" is predetermined such that further movement of the plunger rod 143 and therefore of the plunger 142, in the intake stroke direction causes the locking member 148 to move relative to and towards the contoured portion 152 since the locking member 148 frictionally contacts the inside surface of the body 141. The distance "E" is sufficient to allow for aspiration testing of the syringe. When the movement of the plunger 143 exceeds the distance "D" the inclined portion of the locking member 148 is caused to move up the contoured portion 152 so that the snag projections 150 engage the inside surface of the body 141 which prevents further movement of the plunger 142 in the intake stroke direction.

In either the embodiment of FIGS. 12-18, or that of FIGS. 19-25, an excessive pulling force on the plunger 112, 142 after the locking member 118, 148 has engaged the inside surface of the body 111, 141 will result in the separation of the two parts of the plunger rod whereby the first part 133A, 143A and the piston member 114, 144 will be trapped in the body 111, 141.

It will be recognized by persons skilled in the art that numerous variations and modifications may be made to the invention as described above without departing from the scope or spirit of the invention as broadly described.

We claim:

1. A syringe device comprising:
   a generally elongate hollow body slidably containing a plunger end of a plunger in fluid sealing relationship therewith, the hollow body having a first end with a fluid inlet/outlet, and a second end opposite to the first end;
   the plunger further comprising an elongate plunger rod attached at one end thereof to the plunger end and with the other end thereof projecting out form the second end of the hollow body for slidably moving the plunger end along and within the hollow body;
   a guide means formed in, and being integral with, the plunger rod and which extends along the plunger rod; and
   a locking member which is received in and guided by the guide means, which has at least one snag projection facing in a direction away from the first end of the body and towards the inside surface of the body, and which is in frictional sliding engagement with the inside surface of the body so as to provide for relative movement of the locking member with respect to the guide means; and
   wherein, in use, the guide means functions to maintain the locking member in an unengaged position wherein the snag projection is spaced from an inside surface of the body when the plunger is moved in a first intake stroke away from the first end of the body, and also during a first delivery stroke towards the first end of the body, and the guide means functions to allow relative sliding movement and cause relative pivoting movement of the locking member with respect to the longitudinal axis of the plunger rod such that, upon commencement of a second intake stroke, the locking member snaggingly engages the inside surface of the body to resist further movement of the plunger in the intake stroke direction for preventing reuse of the syringe device.

2. A syringe device comprising:
   a generally elongate hollow body slidably containing a plunger end of a plunger in fluid sealing relationship therewith, the hollow body having a first end with a fluid inlet/outlet, and a second end opposite to the first end;

the plunger further comprising an elongate plunger rod having one end thereof attached to the plunger end and the other end thereof projecting out from the second end of the hollow body for slidably moving the plunger end along and within the hollow body;

a guide means formed in, and being integral with, the plunger rod and which extends along the plunger rod; and a locking member which is received in and guided by the guide means, which has at least one snag projection facing in a direction away from the first end of the body and towards the inside surface of the body, and which is in frictional sliding engagement with the inside surface of the body so as to provide for relative movement of the locking member with respect to the guide means;

wherein the guide means has a first stop means against which the locking member bears during the first intake stroke;

a second stop means spaced from said first stop means and against which the locking member bears during the delivery stroke;

a slide means extending between the first and second stop means along which the locking member slides during use of the syringe device;

wherein the first stop means causes the locking member to be orientated at a first angle with respect to a longitudinal axis of the plunger rod wherein the snag projection is spaced from the inside surface of the body, the second stop means causes the locking member to be orientated at a second angle with respect to the longitudinal axis which is greater than said first angle, and wherein the snag projection is still spaced from the inside surface of the body, and wherein the guide means further comprises an interference portion which, during a second intake stroke, causes the locking member to pivot further away from the longitudinal axis and thereby snaggingly engage the snag projection against the inside surface of the body to resist further movement of the plunger in the intake stroke direction, but only when the locking member is oriented at least a predetermined angle with respect to the longitudinal axis which is larger than the first angle at the commencement of the second intake stroke.

3. The syringe device of claim 2 wherein the interference portion is positioned intermediate the first and second stop means and is spaced a predetermined distance from the second stop means so as to allow for aspiration testing of the syringe device.

4. A syringe device comprising:

a generally elongate hollow body slidably containing a plunger end of a plunger in fluid sealing relationship therewith, the hollow body having a first end with a fluid inlet/outlet, and a second end opposite the first end;

the plunger further comprising an elongate plunger rod having one end thereof attached to the plunger end and with the other end thereof projecting out from the second end of the hollow body for slidably moving the plunger end along within the hollow body;

a guide means formed in, and being integral with, the plunger rod and which extends along the plunger rod; and a locking member which is received in and guided by the guide means, which as at least one snag projection facing in a direction away from the first end of the body and towards the inside surface of the body, and which is in frictional sliding engagement with the inside surface of the body so as to provide for relative movement of the locking member with respect to the guide means;

wherein the guide means comprises:

an elongate slide means extending longitudinally of the plunger rod;

a first stop means at one end of the slide means; a contoured portion at a predetermined position along the slide means; and a second stop means at the other end of the slide means;

the device further comprising a sleeve member which cooperates with the plunger rod, whereby, in use, the sleeve member overhangs and retains the locking member adjacent the first stop means during the first intake stroke, the locking member bears against the first stop means during the delivery stroke whilst the sleeve member is caused to move relative to the plunger rod away from the guide means and release the locking member; and, at the commencement of the second intake stroke, the locking member is caused to slide along the slide means such that a portion thereof rides up an inclined face of the contoured portion and is caused to pivot with respect to the longitudinal axis of the plunger rod (and brings) whereby the snag projection is brought into snagging engagement with the inside surface of the hollow body to resist further movement of the plunger in the intake stroke direction.

5. The syringe device of claim 4 wherein the sleeve member is caused to move in unison with the plunger and to retain the locking member during the first intake stroke, and, due to a frictional engagement of the sleeve member with the inside surface of the body, is caused to move with respect to and along the plunger rod away from the plunger end so as to release the locking member when the plunger is moved in the delivery stroke.

6. The syringe device of claim 5 wherein the inclined surface is inclined with respect to a plane of the slide means along which a base portion of the locking member slides during a second intake stroke of the plunger, wherein the inclined surface guides the base portion of the locking member such that the snag projection is moved into snagging engagement with the inside surface of the body, and wherein the inclined surface has a leading edge in the plane of the slide means which is spaced a predetermined distance from the first stop means which is sufficient to allow for aspiration testing of the syringe device.

7. The syringe device of claim 2 wherein the plunger rod is formed by two or more member which cooperate and, in combination, define the guide means for receiving and guiding the locking member.

8. The syringe device of claim 7 wherein the plunger rod is formed by two members which are slidable with respect to one another in the longitudinal direction of the plunger rod between a retracted position wherein the locking member is retained between the first stop means of the first member and a surface of the second member which is generally parallel to the first stop means, and an extended position wherein the surface of the second member is spaced from the guide means;

wherein the two plunger rod members are in their retracted position before a first intake stroke, and are moved into their extended position during the first intake stroke; and wherein the plunger rod members have a securing means adapted to secure the tow plunger rod members together in their extended position before commencement of the delivery and second intake strokes.

9. The syringe device of claim 8 wherein the interference portion is positioned intermediate the first and second stop means and is spaced a predetermined distance from the second stop means so as to allow for aspiration testing of they syringe device.

10. A syringe device comprising:

a generally elongate hollow body slidably containing a plunger end of a plunger in fluid sealing relationship therewith, the hollow body having a first end with a fluid inlet/outlet, and a second end opposite to the first end;

the plunger further comprising an elongate plunger rod attached at one end thereof to the plunger end and with the other end thereof projecting out from the second end of the hollow body for slidably moving the plunger end along and within the hollow body;

a guide means formed in, and being integral with, the plunger rod; and a locking member which is received in and guided by the guide means, which has at least one snag projection facing in a direction away from the first end of the body and towards the inside surface of the body, and which is in frictional sliding engagement with the inside surface of the body so as to provide for relative movement of the locking member with respect to the guide means;

wherein the plunger rod is formed by a first member and a second member which cooperate and, in combination, define the guide means for receiving and guiding the locking member, wherein:

the plunger rod members are slidable with respect to one another in the longitudinal direction of the plunger rod between a retracted position and an extended position;

the first plunger member has an overhand portion and the second plunger member has a contoured portion, with the first and second plunger members, in combination, forming an elongate slide means;

the locking member has a hook portion at one end thereof which is closest to the first end of the body, a base portion spaced from the hook portion, with the snag projection being at the other end of the locking member opposite to the one end; and wherein, in use, the first and second plunger members are initially in the retracted position with the locking member wedged between the overhang portion and the slide means and the hook portion; whereby, during a first intake stroke, the contoured portion moves towards, under and past the hook portion of the locking member whilst the plunger rod members move to their extended position; and, during a subsequent delivery stroke, the contoured portion moves back towards the hook portion and an edge of the contoured portion is engaged with the hook portion whereafter the locking member is caused to be disengaged from between the overhang portion and the slide means and is moved forwards towards the plunger end along the slide means whilst the plunger members move back towards their retracted position; and, during a second intake stroke, the contoured portion moves rearwardly relative to the locking member and causes the base portion of the locking member to ride up an inclined surface of the contoured portion so that the snag projection snaggingly engages with the inside surface of the hollow body whereby the plunger is prevented from further movement in the intake stroke direction.

11. The syringe device of claim 10 wherein a distance between the base portion of the locking member and the contoured portion of the guide means, in the positions of the plunger rod and locking member after the second intake stroke has been commenced and the plunger rod members are just in their extended position, is sufficient to allow for aspiration testing of the syringe device.

* * * * *

UNITED STATES PATENT AND TRADEMARK OFFICE
CERTIFICATE OF CORRECTION

PATENT NO. : 5,290,235
DATED : March 1, 1994
INVENTOR(S) : Polyblank et al.

It is certified that error appears in the above-identified patent and that said Letters Patent is hereby corrected as shown below:

Col. 14, line 4, " "D" " should be --"E"--.

Col. 14, line 15, "133A" should be --113A--.

Col. 14, line 31, "form" should be --from--.

Col. 16, line 57, "member" should be --members--.

Col. 17, line 6, "tow" should be --two--.

Signed and Sealed this

Second Day of August, 1994

Attest:

BRUCE LEHMAN

*Attesting Officer*     *Commissioner of Patents and Trademarks*